US009642856B2

(12) United States Patent
Hedley et al.

(10) Patent No.: US 9,642,856 B2
(45) Date of Patent: May 9, 2017

(54) TREATMENT FOR PANCREATIC CANCER

(71) Applicant: University Health Network, Toronto (CA)

(72) Inventors: David W. Hedley, Toronto (CA); Ines Lohse, Toronto (CA); Jacqueline M. Mason, Toronto (CA); Mark R. Bray, Oakville (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 15/029,269

(22) PCT Filed: Oct. 3, 2014

(86) PCT No.: PCT/CA2014/050952
§ 371 (c)(1),
(2) Date: Apr. 14, 2016

(87) PCT Pub. No.: WO2015/054781
PCT Pub. Date: Apr. 23, 2015

(65) Prior Publication Data
US 2016/0250220 A1    Sep. 1, 2016

Related U.S. Application Data

(60) Provisional application No. 61/892,887, filed on Oct. 18, 2013.

(51) Int. Cl.
| | |
|---|---|
| A61K 31/5377 | (2006.01) |
| A61K 31/416 | (2006.01) |
| A61P 35/00 | (2006.01) |
| C07D 413/14 | (2006.01) |
| A61K 45/06 | (2006.01) |
| A61K 31/7068 | (2006.01) |
| A61K 33/24 | (2006.01) |

(52) U.S. Cl.
CPC ...... *A61K 31/5377* (2013.01); *A61K 31/7068* (2013.01); *A61K 33/24* (2013.01); *A61K 45/06* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 4,642,309 A | 2/1987 | Michel et al. | |
| 5,182,397 A | 1/1993 | Condon et al. | |
| 6,506,763 B2 | 1/2003 | Tang et al. | |
| 7,148,249 B2 | 12/2006 | Kley et al. | |
| 7,205,328 B2 | 4/2007 | He et al. | |
| 7,429,609 B2 | 9/2008 | Ohi et al. | |
| 8,263,596 B2 | 9/2012 | Sampson et al. | |
| 8,481,525 B2 | 7/2013 | Sampson et al. | |
| 8,481,533 B2 | 7/2013 | Sampson et al. | |
| 8,765,748 B2 | 7/2014 | Pauls et al. | |
| 8,921,545 B2 | 12/2014 | Cumming et al. | |
| 8,933,070 B2 | 1/2015 | Pan et al. | |
| 8,999,968 B2 | 4/2015 | Sampson et al. | |
| 9,139,563 B2 | 9/2015 | Sampson et al. | |
| 9,402,828 B2 | 8/2016 | Pan et al. | |
| 2007/0135509 A1 | 6/2007 | Blackburn et al. | |
| 2009/0054397 A1 | 2/2009 | Ohi et al. | |
| 2011/0065702 A1 | 3/2011 | Pauls et al. | |
| 2012/0149686 A1 | 6/2012 | Sampson et al. | |
| 2014/0045822 A1 | 2/2014 | Sampson et al. | |
| 2015/0133677 A1 | 5/2015 | Cumming et al. | |
| 2016/0045511 A1 | 2/2016 | Sampson et al. | |

FOREIGN PATENT DOCUMENTS

| | | |
|---|---|---|
| CA | 2383623 A1 | 2/2000 |
| CA | 2498781 A1 | 4/2004 |
| CA | 2690567 A1 | 12/2008 |
| CA | 03101968 A1 | 4/2009 |

(Continued)

OTHER PUBLICATIONS

International Search Report and Written Opinion for International Application No. PCT/CA2014/050952 mailed Dec. 9, 2014.
Lohse et al., The PLK-4 inhibitor CFI-400945 reduces tumor growth in patient-derived pancreatic xenografts, AACR-NCI-EORTC International Conference on Molecular Targets and Cancer Therapeutics, Oct. 7, 2013, Boston, Abstract No. 282.
International Search Report for International Application No. PCT/CA2008/002227 mailed Apr. 6, 2009.
International Search Report for International Application No. PCT/CA2011/000386 mailed Aug. 2, 2011.
International Search Report for International Application No. PCT/CA2010/000518 mailed Jul. 8, 2010.
Lin et al., "Synthesis and biological evaluation of 3-ethylidene-1,3-dihydro-indol-2-ones as novel checkpoint 1 Inhibitors", Bioorganic & Medicinal Chemistry Letter, vol. 16, pp. 421-426 (2006).

(Continued)

*Primary Examiner* — Kristin Vajda
(74) *Attorney, Agent, or Firm* — McCarter & English, LLP; Steven G. Davis; Wei Song

(57) ABSTRACT

The invention is related to a method of treating a subject with pancreatic cancer with administration of a compound represented by Structural Formula (I): or a pharmaceutically acceptable salt thereof.

15 Claims, 2 Drawing Sheets

(56) References Cited

FOREIGN PATENT DOCUMENTS

| CA | 2709536 | A1 | 7/2009 |
|---|---|---|---|
| CA | 2756568 | A1 | 10/2010 |
| CA | 2781839 | A1 | 6/2011 |
| JP | 2002522452 | A | 7/2002 |
| JP | 2003535847 | A | 12/2003 |
| JP | 2009173629 | A | 8/2009 |
| WO | 9632380 | A1 | 10/1996 |
| WO | 9640116 | A1 | 12/1996 |
| WO | 9807695 | A1 | 2/1998 |
| WO | 9910325 | A1 | 3/1999 |
| WO | 0056709 | A1 | 9/2000 |
| WO | 0153268 | A2 | 7/2001 |
| WO | 0210137 | A2 | 2/2002 |
| WO | 2004037247 | A1 | 5/2004 |
| WO | 2005058309 | A1 | 6/2005 |
| WO | 2007008664 | A1 | 1/2007 |
| WO | 2007058626 | A1 | 5/2007 |
| WO | 2009079767 | A1 | 7/2009 |
| WO | 2009111868 | A1 | 9/2009 |
| WO | 2009124692 | A1 | 10/2009 |
| WO | 2009132774 | A1 | 11/2009 |
| WO | 2010000518 | A1 | 7/2010 |
| WO | 2010115279 | A1 | 10/2010 |
| WO | 2011115279 | A1 | 9/2011 |
| WO | 2011123946 | A1 | 10/2011 |
| WO | 2012048411 | A1 | 4/2012 |
| WO | 2012118812 | A2 | 9/2012 |

OTHER PUBLICATIONS

Zhu et al., "Discovery and SAR of oxindole-pyridine-based protein kinase B/Akt inihibitors for treating cancers", Bioorganic & Medicinal Chemistry Letters, vol. 16, pp. 3424-3429 (2006).

Hauf et al., "The small molecule Hesperadin reveals a role for Aurora B in correcting kinetochore-microtubule attachment and in maintaining the spindle assembly checkpoint", The Journal of Cell Biology, vol. 161, No. 2, pp. 281-294 (2003).

Sessa et al., Mechanism of Aurora B Activation by INCENP and Inhibitaion by Hesperadin Molecular Cell, vol. 18, 379-391, Apr. 29, 2005.

Moshinsky et al., "SU9516: biochemicalanalysis of cdk inihibition and crystal structure in complex with cdk2", Biochemical and Biophysical Research Communications, vol. 310, pp. 1026-1031 (2003).

Howard et al., "Synthesis and aldose reductase inhibitory activity of substituted 2(1H)-benzimidazolone- and oxindole-1-acetic acids", Eur J Med Chem, vol. 27, pp. 779-789 (1992).

Rellos et al., "Structure and Regulation of the Human Nek2 Centrosomal Kinase", The Journal of Biological Chemistry, vol. 282, No. 9, pp. 6833-6842 (2007).

Guan et al., "Design and synthesis of aminopropyl tetrahydroindole-based indolin-2-ones as selective and potent Inhibitors of Src and Yes tyrosine kinase", Bioorganic & MedicinalChemistry Letters, vol. 14, pp. 187-190 (2004).

Adams et al., "Mapping the Kinase Domain of the Janus Kinase 3", Bioorganic & Medicinal Chemistry Letters, vol. 13, pp. 3105-3110 (2003).

Mohammadi et al., "Structures of the Tyrosine Kinase Domain of Fibroblast Growth Factor Receptor in Complex Inhibitors", Science, vol. 276, 955 (1997).

Johnson et al., "Pharmacological and Functional Comparison of the Polo-like Kinase Family: Insight into Inhibitor and Substrate Specificity", American Chemical Society (2007).

Moldvai et al., "Synthesis of Spiro[cyclopropone-1,3'[3H]indol]-2'(1'H)-ones with Antihypoxic Effects", Arch. Pharm. Pharm. Med. Chem. (1996).

Jiang et al., "Design, synthesis, and biological evaluations of novel oxindoles as HIV-1 non-nulceoside reverse transcriptase inhibitors. Part 2", Bioorganic & Medicinal Chemistry Letters, vol. 16, pp. 2109-2112 (2006).

Golub et al. Science (1999) vol. 286 531-537.

Lala et al. Cancer and Metastasis Reviews (1998), 17(1), 91-106.

Blackburn et al. Caplus an 2002:594639 2002.

Sharpless, K. Barry; Vicinal Diol Cyclic Sulfates: Like Epoxides Only More Reactive; American Chemical Society 1988; pp. 7538-7539.

Carreira, Erick M. et al., Total Synthesis of (-)-Spirotryprostatin B: Synthesis and Related Studies; J. Am. Chem. Soc. 2005; 127, pp. 11505-11515.

International Search Report mailed Jun. 23, 2011 for PCT/CA2011/000387.

International Preliminary Report on Patentability mailed Oct. 18, 2012 for PCT/CA2011/000387.

Kazazian, Karineh, et al., Polo-like kinase 4 (Plk4) promotes cancer cell invasion, J Am Coll Surg, 217(3):S128, (2013) (Abstract).

TREATMENT FOR PANCREATIC CANCER

RELATED APPLICATIONS

This application is a U.S. national stage application of International Application No. PCT/CA2014/050952, filed Oct. 3, 2014, which claims the benefit of U.S. Provisional Application No. 61/892,887, filed Oct. 18, 2013. The entire teachings of each of the aforementioned applications are incorporated herein by reference.

BACKGROUND

Pancreatic cancer is a malignant neoplasm originating from transformed cells arising in tissues forming the pancreas. Pancreatic cancer is one of the most common causes of cancer-related deaths in the world. Due to the absence of specific symptoms, the lack of early detection techniques, and highly aggressive phenotypes, pancreatic cancer is usually diagnosed at an advanced-incurable and metastatic stages. Thus, pancreatic cancer has an extremely poor prognosis: for all stages combined, the 1- and 5-year relative survival rates are 25% and 6%, respectively.

Therefore, there is an urgent need to develop new drugs for treatment of pancreatic cancer.

SUMMARY OF THE INVENTION

Applicants have now discovered that compounds of structural formula (I) have potent anticancer activity against pancreatic cancer cells in cell culture (Example 1) and in patient-derived primary pancreatic cancer xenografts (Examples 2 and 4). Based on these discoveries, methods of treating pancreatic cancer with compounds of structural formula (I) are disclosed herein.

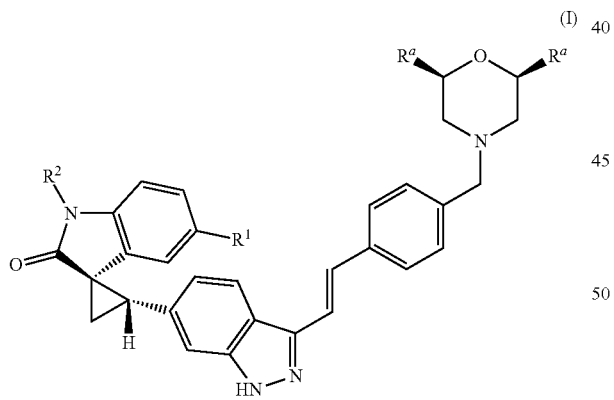

(I)

One embodiment of the invention is a method of treating a subject with pancreatic cancer, comprising administering an effective amount of a compound of structural formula (I), or a pharmaceutically acceptable salt thereof, wherein:

each $R^a$ is independently —H or methyl;

$R^1$ is —H, or methoxy; and $R^2$ is —H, or methyl.

Another embodiment of the invention is the use of a compound represented by structural formula (I) or a pharmaceutically acceptable salt thereof for the manufacture of a medicament for treating a subject with pancreatic cancer.

Another embodiment of the invention is a compound represented by structural formula (I) or a pharmaceutically acceptable salt thereof for treating a subject with pancreatic cancer.

BRIEF DESCRIPTION OF THE DRAWINGS

FIG. 2(A) shows tumor initiating cells (TICs) have a range of hypoxia and growth pattern. FIG. 2(B) shows significant difference in TIC content. FIG. 2(C) is a schematic overview of the limiting dilution assay. FIGS. 2(C) and 2(D) show that Compound II treatment reduced the number of TICs in OCIP51.

DETAILED DESCRIPTION OF THE INVENTION

Figure 1:
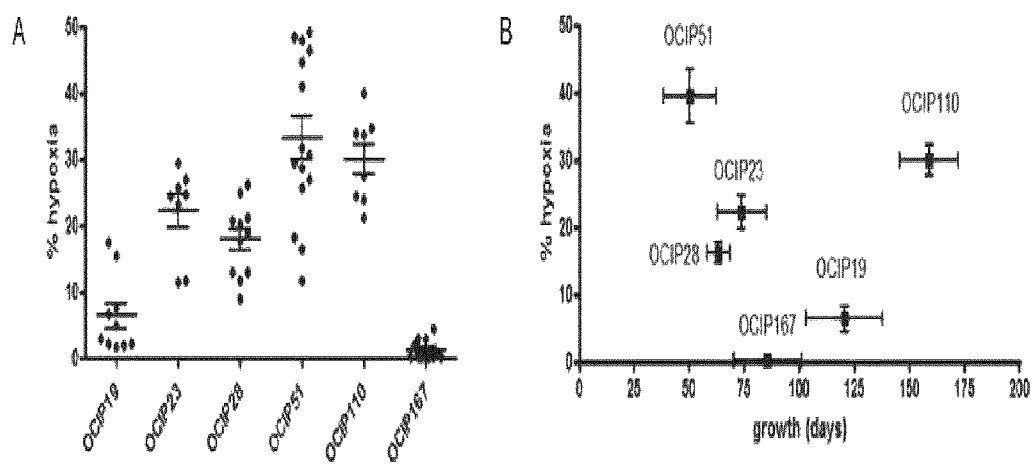
FIGS. 1(A)-(B) are graphs illustrating that patient-derived pancreatic xenograft used in the present invention display a wise range of tumor hypoxia and growth rate.

In one embodiment, the present invention is directed to a method of treating a subject with pancreatic cancer, comprising administering an effective amount of a compound represented by the following structural formula:

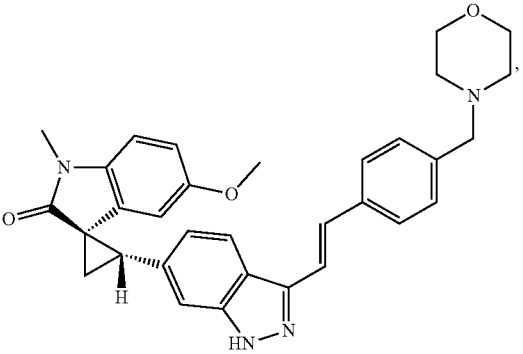 [SMILES: COc1ccc2c(c1)[C@]1(C[C@H]1c1ccc3c(/C=C/c4ccc(CN5CCOCC5)cc4)n[nH]c3c1)C(=O)N2C]

or a pharmaceutically acceptable salt thereof.

Alternatively, the compound is represented by a structural formula selected from

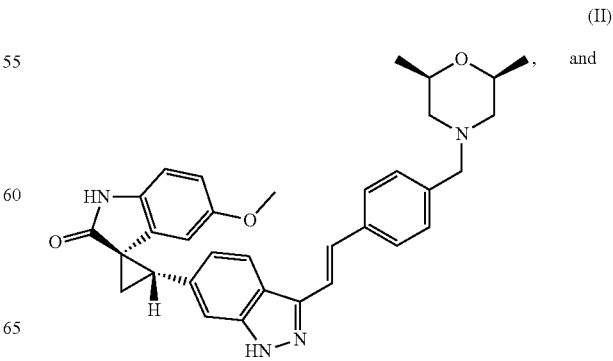

(II)

and

-continued (III)

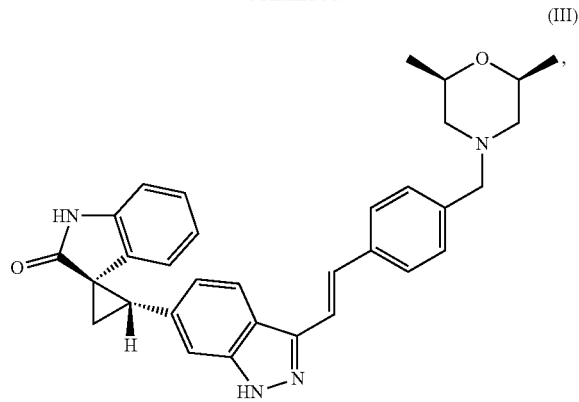

or a pharmaceutically acceptable salt thereof.

Another embodiment of the present invention is a method of treating a subject with pancreatic cancer, comprising administering an effective amount of a compound described above or a pharmaceutically acceptable salt thereof, wherein the pancreatic cancer is an exocrine tumor. Alternatively, the pancreatic cancer is a neuroendocrine tumor.

The exocrine tumor is selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

The neuroendocrine tumor is selected from the group consisting of gastrinoma (Zollinger-Ellison Syndrome), glucagonoma, insulinoma, nonfunctional islet cell tumor, somatostatinoma, and vasoactive intestinal peptide-releasing tumor (VIPoma or Verner-Morrison Syndrome).

In a particular embodiment, the method described above is used for treating a subject with pancreatic cancer, wherein the pancreatic cancer is adenocarcinoma. In another particular embodiment, the pancreatic cancer is hypoxic. In still another particular embodiment, the pancreatic cancer is non-hypoxic.

The compounds used in the present invention include both the neutral form as well as pharmaceutically acceptable salts thereof.

The compounds used in the disclosed methods have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids).

Acids with two or more acidic functional groups can form acid addition salts in varying ratios with the compounds used in the disclosed methods. For example, fumaric, maleic, malic and tartaric acids each have two carboxylic acid functional groups and can form acid addition salts in a ratio of 1:1 or 2:1 acid to the compound, e.g., 1:1 fumaric acid to the compound; 1:1 tartaric acid to the compound; 1:2 maleaic acid to the compound etc.

The term "compound" in reference to the compounds used in the disclosed methods includes solvates (such as disclosed in U.S. Provisional Application No. 61/892,564) and unsolvate form, i.e., there is substantially no solvent in the solid or crystal form of the compound (e.g., less that 10% by weight) and/or no definite ratio of a solvent molecule and the compound molecule in the crystal structure.

The compounds used in the disclosed methods are stereoisomers. Stereoisomers are compounds which differ only in their spatial arrangement.

The stereoisomeric purity of the compounds used in the disclosed methods are at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In some embodiments, the present teachings provide methods of inhibiting the growth of tumor-initiating cells or reducing the likelihood of recurrence of pancreatic cancer in a subject who is undergoing an anti-cancer therapy. The method comprises the steps of:

a) assessing the subject to determine whether pancreatic cancer is in remission; and b) if the pancreatic cancer is in remission; then administering to the subject an effective amount of a compound represented by Structural Formula (I) or a pharmaceutically acceptable salt thereof. If the pancreatic cancer is not in remission, the method optionally further comprises the step of continuing the anti-cancer therapy until the cancer goes into remission and then the step b) of administering an effective amount of a compound represented by Structural Formula (I) or a pharmaceutically acceptable salt thereof.

As used herein, the term "tumor-initiating cells" or "TICs" refer to cells present within some tumors that possess the ability to self-renew and proliferate. These cells are sometimes called cancer stem cells (CSCs) and may be observed to share certain characteristics with normal stem cells, including a stem cell-like phenotype and function. In some embodiments, TICs are characterized by their ability to form tumors after xenotransplantation in immunodeficient mice.

In some embodiments, the present teachings provide methods of inhibiting the growth of tumor-initiating cells or reducing the likelihood of recurrence of pancreatic cancer in a subject whose pancreatic cancer is in remission comprising administering to the subject an effective amount of a compound represented by Structural Formula (I) or a pharmaceutically acceptable salt thereof.

In some embodiments, e.g., where the subject is being treated to reduce the likelihood of recurrence of pancreatic cancer, the subject has already been treated with an anti-cancer therapy. Alternatively, the subject has already been treated with an anti-cancer therapy and the subject is in remission.

Suitable methods known in the art can be used for assessing a subject to determine whether the cancer is in remission. For example, the size of the tumor and/or tumor markers, usually proteins associated with tumors, can be monitored to determine the state of the cancer. Size of the tumor can be monitored with imaging devices, such as X-ray, MRI, CAT scans, ultrasound, mammography, PET and the like or via biopsy.

In some embodiments, the present teachings provide methods of treating a subject with pancreatic cancer comprising administering to the subject an effective amount of a compound represented by Structural Formula (I) in combination with an effective anti-cancer therapy.

In one embodiment, the methods of treating a subject with pancreatic cancer as described above, further comprises co-administering an additional therapeutic agent. In a particular embodiment, the additional therapeutic agent is an anti-cancer drug, for example, Gemcitabine or Cisplatin.

For methods described herein, e.g., coadministration methods, the anti-cancer therapy is selected from the group consisting of surgery, radiation therapy, immunotherapy, endocrine therapy, gene therapy and administration of an anti-cancer agent. Alternatively, the anti-cancer therapy is radiation therapy. In another alternative, the anti-cancer therapy is immunotherapy. In another alternative, the anti-cancer therapy is administration of an anti-cancer agent. In yet another alternative, the anti-cancer therapy is surgery.

Radiation therapy is the use of radiation to kill, destroy or treat the cancers. Exemplary radiation therapy includes, but is not limited to, gamma-radiation, neutron beam radiotherapy, electron beam radiotherapy, proton therapy, brachytherapy, and radioisotope therapy (i.e., systemic radioactive isotopes therapy).

An endocrine therapy is a treatment that adds, blocks or removes hormones. For example, chemotherapeutic agents that can block the production or activity of estrogen have been used for treating breast cancer. In addition, hormonal stimulation of the immune system has been used to treat specific cancers, such as renal cell carcinoma and melanoma. In one embodiment, the endocrine therapy comprises administration of natural hormones, synthetic hormones or other synthetic molecules that may block or increase the production of the body's natural hormones. In another embodiment, the endocrine therapy includes removal of a gland that makes a certain hormone.

As use herein, a gene therapy is the insertion of genes into a subject's cell and biological tissues to treat diseases, such as cancer. Exemplary gene therapy includes, but is not limited to, a germ line gene therapy and a somatic gene therapy.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Alternatively, the anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agent suitable for use in the methods described herein include any anti-cancer agents that have been approved for the treatment of cancer. In one embodiment, the anti-cancer agent includes, but is not limited to, a targeted antibody, an angiogenisis inhibitor, an alkylating agent, an antimetabolite, a vinca alkaloid, a taxane, a podophyllotoxin, a topoisomerase inhibitor, a hormonal antineoplastic agent and other antineoplastic agents.

In one embodiment, the anti-cancer agents that can be used in methods described herein include, but are not limited to, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin and adriamycin and a combination thereof.

In one embodiment, the anti-cancer agent and the compound represented by Structural Formula (I) are administered contemporaneously. When administered contemporaneously, the anti-cancer agent and the compound can be administered in the same formulation or in different formulations. Alternatively, the compound and the additional anti-cancer agent are administered separately at different times.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

The term "inhibiting the growth of tumor-initiating cells" refers to preventing or decreasing the rate of the proliferation and/or survival of the tumor-initiating cells.

As used herein, the term "reducing the likelihood of recurrence of a cancer" means inhibiting or delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

As used herein, "treating a subject with pancreatic cancer" includes achieving, partially or substantially, one or more of the following: arresting the growth, reducing the extent of the pancreatic cancer (e.g., reducing size of a tumor), inhibiting the growth rate of the cancer, ameliorating or improving a clinical symptom or indicator associated with the pancreatic cancer (such as tissue or serum components) or increasing longevity of the subject; and reducing the likelihood of recurrence of the pancreatic cancer.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with pancreatic cancer or reducing the likelihood of recurrence of pancreatic cancer), a "treatment" or dosing regime of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds used in the disclosed methods can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds used in the disclosed methods can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound used in the disclosed methods may be incorporated with excipient and used in the form of ingestible tablets, buccal tablets, troches, capsules, elixirs, suspensions, syrups, wafers, and the like.

Typically for parenteral administration, solutions of a compound used in the disclosed methods can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound used in the disclosed methods for the extemporaneous preparation of sterile injectable solutions or dispersions are appropriate.

For nasal administration, the compounds used in the disclosed methods can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds used in the disclosed methods can be formulated with a carrier such as sugar, acacia, tragacanth, or gelatin and glycerine, as tablets, lozenges or pastilles.

For rectal administration, the compounds used in the disclosed methods can be formulated in the form of suppositories containing a conventional suppository base such as cocoa butter.

The compounds used in the disclosed methods may be prepared by methods disclosed in U.S. Pat. Nos. 8,263,596; 8,481,525; and 8,481,533; and U.S. Patent Application Publication No. 2013-0096301 A1. The corresponding pharmaceutically acceptable salts, solvates, as well as crystal forms thereof may be prepared by methods disclosed in U.S. Provisional Application No. 61/892,564.

The invention is illustrated by the following examples which are not intended to be limiting in any way.

EXEMPLIFICATION

Example 1

Growth Inhibition (GI50) Assay

BxPC-3 and PANC-1 cell lines were obtained from American Type Culture Collection (ATCC, Manassas, Va.) and maintained according to the supplier's instructions. Short tandem repeat (STR) profiling was used to verify authenticity of the cell lines. Sixteen STR loci were simultaneously amplified in a multiplex PCR reaction (The Hospital for Sick Children, Toronto, Canada), and the ATCC database was used for comparison, where possible. Cell lines were routinely tested for mycoplasma and used at low passage numbers (<15).

Cells were seeded at 3000 per 80 µL, into 96-well plates according to cell growth rate 24 hours before compound overlay and cultured at 37° C. and 5% CO2. Compounds were prepared as 10 mM stocks in 100% DMSO. Each 10 mM stock was diluted with DMEM (Dulbecco's Modified Eagle's Medium) cell growth medium (Invitrogen, Carlsbad, Calif.) containing 10% FBS (fetal bovine serum) such that the final concentrations ranged from 500 nM to 250 µM. Aliquots (20 µL) from each concentration were overlaid the aid of a Tecan Freedom EVO robotic workstation (Tecan, Mannedorf, Switzerland) to 80 µL of pre-seeded cells to achieve final concentrations of 100 nM to 50 µM. After 5 days, cell growth in each well was assessed by the sulforhodamine B (SRB) assay measuring total protein content. The cells were fixed in situ by gently removing the culture media and adding 50 µL of ice-cold 10% Tri-chloroacetic Acid (TCA) per well and incubation at 4° C. for 30 minutes. The plates were washed with water five times and allowed to air dry for 5 minutes. 50 µL of 0.4% (w/v) SRB (Sigma, St. Louis, Mo.) solution in 1% (v/v) acetic acid was added to each well followed by incubation for 30 minutes at room temperature. The plates were washed four times with 1% acetic acid to remove unbound SRB and air dried for 5 minutes. The SRB was solubilized with 100 µL of 10 mM Tris pH 10.5 per well, and absorbance was read at 570 nm using a SpectraPlus microplate reader (Molecular Devices Corporation). SRB absorbance values were adjusted by subtracting the average of the baseline readings from untreated cells assessed one day after cell seeding. The percentage (%) of relative inhibition of cell growth was calculated by comparing to DMSO-treated cells. GI50s were calculated using GraphPad PRISM software (GraphPad Software Inc., San Diego, Calif.).

GI50s for Compound II against Human Pancreatic Cancer Cell Lines:

Cell Line: BxPC-3 (KRas wild-type, TP53 mutant, CDKN2A wild-t e SMAD4 homozygous deletion); Compound II GI50=0.015 µM Cell Line: PANC-1 (KRas mutant, TP53 mutant, CDKN2A homozygous deletion, SMAD4 wild-type); Compound II 5 GI50=0.025 µM Example 2

Compound II Inhibits Tumor Growth in Patient-Derived Pancreatic Xenograft Model 6 orthotopically implanted patient-derived pancreatic xenograft models with varying growth rates and levels of tumor hypoxia were used in order to investigate the efficiency of the Compound II as a mono-therapy or in combination with Gemcitabine.

The patient-derived pancreatic xenograft models were established by attaching a piece of the patient tumor on the pancreas of 4-5 week old Non-obese diabetic (NOD)/Severe combined immunodeficiency (SCID) mice. The xenograft models closely resemble the morphology of the patient specimen and represent the range of tumor morphologies described in pancreatic cancer patients.

Tumor volume was evaluated by palpation and animals were randomized into treatment groups. Animals were treated with Compound II using a daily dose of 7.5 mg/kg by oral gavage for 21 days for experiments evaluating activity as a mono-therapy, or with 13.5 mg/kg according to a 2-day-on-5-days-off schedule in combination bi-weekly 100 mg/kg Gemcitabine for 21 days.

Tumor weight after completion of the treatment and overall survival were evaluated. Immunofluorescence (IF) staining of xenograft sections was used to evaluate tumor hypoxia and proliferation. The impact of Compound II treatment on survival was examined in 6 animals per group. Mice were followed until the animals either died or had to be euthanized due to oversized tumors. The results show significantly decreased tumor weight in 4 of the 6 tested models and resulted in increased survival.

FIG. 1(A) shows that the magnitude of tumor hypoxia was evaluated using the 2-nitroimidazole hypoxia marker EF5 by Immunohistochemistry. While the xenograft models significantly differ in the magnitude of tumor hypoxia, little variance was observed in tumors of the same model. FIG. 1(B) shows that growth rate was established as the time elapsed between two passages. Tumor morphology, magnitude of hypoxia and growth rate were stable over the course of multiple passages. Error bars represent SEM.

Treatment with Compound II as a mono-therapy for 21 days significantly reduced tumor weight in 4 of the 6 tested patient-derived pancreatic xenograft models and an increase in overall survival in a number of responsive models. The strongest response to Compound II treatment was observed in the highly hypoxic fast growing xenograft models OCIP51 where medium survival was 103 days in the treatment group when compared to 54 days in vehicle treated animals.

The correlation between tumor hypoxia, proliferation and response to Compound II treatment were further examined in order to establish biological correlates for treatment response. Preliminary results show that although tumor weight was reduced in most of the tested models, the strongest response to Compound II as a mono-therapy was observed in highly hypoxic models when compared to medium or low hypoxic models.

Example 3

Compound II Reduces Number of Tumor Initiating Cells (TIC) in OCIP51

Figure 2:
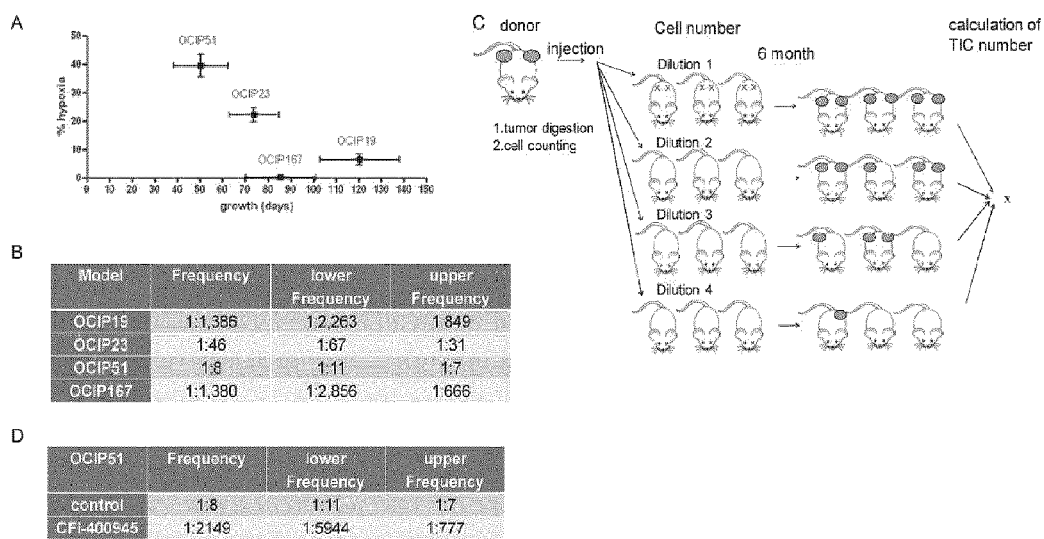
FIGS. 2(A)-(D) are graphs illustrating that Compound II reduces Number of Tumor Initiating Cells (TIC) in OCIP51.

FIG. 2 shows that Compound II treatment on Tumor Initiating Cells (TICs) displays a (A) range of hypoxia and growth pattern and (B) significantly differ in TIC content. FIG. 2(C) is a schematic overview of the limiting dilution assay. Briefly, xenograft tumors were grown to a diameter of approximately 1 cm and treated with 52 mg/kg Compound II and tumors harvested 12 h after treatment. Excised tumors were mechanically minced and a single cell suspension prepared using a DNAse, Collagenase and Protease cocktail. A sample of the single cell suspension was stained for mouse CD31-FITC and H2K-FITC to establish the mouse cell content. Cells were counted using a haemocytometer and the human content was calculated. 3-6 dilutions of human cells per sample were injected into the flank of NOD/SCID mice. 3 mice were injected into both flanks per dilution. Tumor take rate was observed over the course of 6 month. Tumor initiating frequency was calculated from using the L-Calc software. As indicated in FIG. 2(D), preliminary results show that Compound II treatment reduced the number of TICs in OCIP51. The remaining 3 xenograft models have been injected for the dilutions.

Example 4

Treatment with Compound II in Combination with Cisplatin Reduces Tumor Growth

OCIP110 tumors were implanted orthotopically onto the pancreas of 4-5 week old SCID mice. Tumor volume was evaluated by palpation and animals were randomized into treatment groups. Animals were treated with either Compound II on a 2-on/5-off schedule with 10 mg/kg, a weekly dose of 4 mg/kg Cisplatin or the combination treatment for 21 days. Tumor weight was evaluated when tumors were excised at the end of the treatment. Treatment with Compound II alone reduced tumor weight although the efficiency in the 2-on/5-off schedule appears to be lower than on the daily treatment. Treatment with the combination of Compound II and Cisplatin however did not further decrease tumor weight when compared to the single treatment.

What is claimed is:

1. A method of treating a subject with pancreatic cancer, comprising administering an effective amount of a compound of structural formula (I):

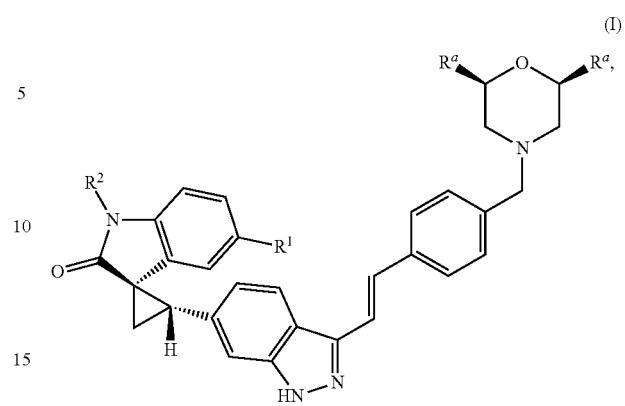

or a pharmaceutically acceptable salt thereof, wherein:
each $R^a$ is independently —H or methyl;
$R^1$ is —H, or methoxy; and
$R^2$ is —H, or methyl.

2. The method of claim 1, wherein the compound is represented by the following structural formula:

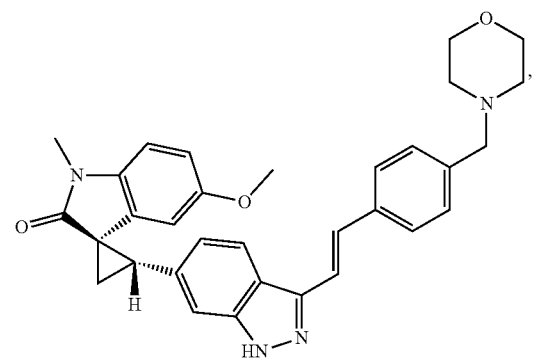 [SMILES: COc1ccc2c(c1)[C@]1(C[C@H]1c1ccc3c(/C=C/c4ccc(CN5CCOCC5)cc4)n[nH]c3c1)C(=O)N2C]

or a pharmaceutically acceptable salt thereof.

3. The method of claim 1, wherein the compound is represented by the following structural formula:

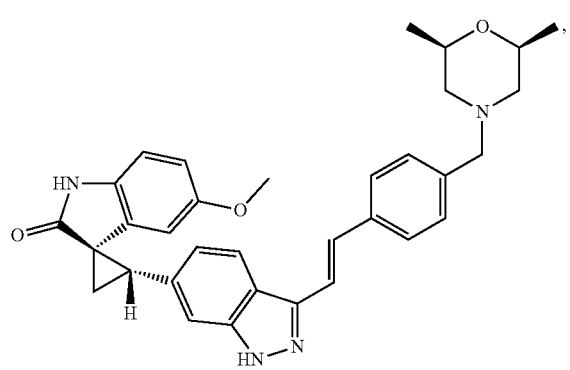 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

or a pharmaceutically acceptable salt thereof.

4. The method of claim 1, wherein the compound is represented by the following structural formula:

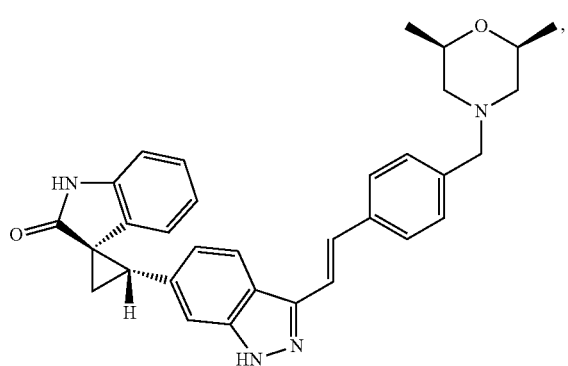 [SMILES: C[C@@H]1CN(Cc2ccc(/C=C/c3n[nH]c4cc([C@@H]5C[C@@]56C(=O)Nc5ccccc56)ccc34)cc2)C[C@H](C)O1]

or a pharmaceutically acceptable salt thereof.

5. The method of claim 1, wherein the pancreatic cancer is an exocrine tumor.

6. The method of claim 1, wherein the pancreatic cancer is a neuroendocrine tumor.

7. The method of claim 5, wherein the exocrine tumor is selected from the group consisting of acinar cell carcinoma, adenocarcinoma, adenosquamous carcinoma, giant cell tumor, intraductal papillary-mucinous neoplasm (IPMN), mucinous cystadenocarcinoma, pancreatoblastoma, serous cystadenocarcinoma, and solid and pseudopapillary tumors.

8. The method of claim 6, wherein the neuroendocrine tumor is selected from the group consisting of gastrinoma (Zollinger-Ellison Syndrome), glucagonoma, insulinoma, nonfunctional islet cell tumor, somatostatinoma, and vasoactive intestinal peptide-releasing tumor (VIPoma or Verner-Morrison Syndrome).

9. The method of claim 1, wherein the pancreatic cancer is adenocarcinoma.

10. The method of claim 1, wherein the pancreatic cancer is hypoxic.

11. The method of claim 1, wherein the pancreatic cancer is non-hypoxic.

12. The method of claim 1, further comprising co-administering an additional therapeutic agent.

13. The method of claim 12, wherein the additional therapeutic agent is an anti-cancer drug.

14. The method of claim 13, wherein the anti-cancer drug is Gemcitabine.

15. The method of claim 13, wherein the anti-cancer drug is Cisplatin.

* * * * *